United States Patent [19]

Kalema et al.

[11] Patent Number: 5,254,255
[45] Date of Patent: Oct. 19, 1993

[54] ENHANCED EXTRACTION OF VALERIC ACID OR CAPROIC ACID FROM AQUEOUS MIXTURES

[75] Inventors: William S. Kalema, Kampala, Uganda Uganda; Leon S. Scott, Wilmington, Del.

[73] Assignee: E. I. Du Pont de Nemours and Company, Wilmington, Del.

[21] Appl. No.: 961,323

[22] Filed: Oct. 15, 1992

[51] Int. Cl.$^5$ ............................................. B01D 11/04
[52] U.S. Cl. .................................... 210/634; 210/511
[58] Field of Search ................. 210/634, 511; 562/602

[56] References Cited

U.S. PATENT DOCUMENTS 4,110,372  8/1978  Hey et al. ...................... 562/602 X

Primary Examiner—Frank Spear

[57] ABSTRACT

Extraction of valeric and/or caproic acid from an aqueous solution containing adipic acid and/or methyl glutaric acid using an organic solvent is enhanced by carrying out the process using an extraction-enhancing acid, such as acetic or isobutyric acid, which is soluble in the organic solvent.

9 Claims, No Drawings

ENHANCED EXTRACTION OF VALERIC ACID OR CAPROIC ACID FROM AQUEOUS MIXTURES

FIELD OF INVENTION

This invention relates to an improved process for extracting valeric acid or caproic acid from aqueous solutions also containing adipic acid and/or methyl glutaric acid.

BACKGROUND OF THE INVENTION

In the manufacture of adipic acid by the carbonylation of butadiene using Group VIII catalysts, an aqueous solution containing adipic acid and/or methyl glutaric acid and caproic acid and/or valeric acid is formed. See, for example, Burke U.S. Pat. No. 4,788,333. It is desirable to remove the caproic acid and/or valeric acid from this aqueous solution and obtain an aqueous solution of adipic acid and/or methyl glutaric acid that contains less than about 100 parts per million of caproic and valeric acid.

It has been found that level of valeric acid and caproic acid in such aqueous solutions can be reduced by extraction with certain organic solvents. Although such an organic/aqueous extraction has been found to work well for reducing the level of the caproic or valeric acid in the aqueous phase to about 0.2 wt. %, further purification to 200 ppm or less requires an excessive amount of solvent or number of extractions. A solution to this problem, which dramatically increases the efficiency of residual valeric or caproic acid extraction from aqueous solutions, has now been found.

SUMMARY OF THE INVENTION

A process for removing a monobasic carboxylic acid selected from the group of valeric and caproic acids from an aqueous mixture containing said monobasic carboxylic acid and adipic acid and/or methyl glutaric acid, which comprises extracting said monobasic carboxylic acid from said aqueous mixture by contacting said aqueous mixture with a solvent which comprises a substantially water-immiscible organic solvent and an extraction-enhancing acid soluble in said organic solvent. Suitable organic solvents have 6 to 12 carbons. Mixtures of organic solvents and mixtures of mixtures of extraction-enhancing acids may also be employed.

An "extraction-enhancing acid" is a monocarboxylic acid (other than valeric or caproic acid) having 2 to 10 carbon atoms, a sulfonic acid, a sulfinic acid or a boronic acid. The extraction-enhancing acid must be soluble in the organic solvent in an amount of at least 0.01 wt. % of the weight of the solvent, about 2–3% is often preferred.

DETAILED DESCRIPTION OF THE INVENTION

The process of this invention can be run in batch or continuous mode.

Suitable organic solvents for the process of this invention include $C_6$–$C_{12}$ aliphatic and $C_6$–$C_{12}$ aromatic hydrocarbons and alkyl, halo- or alkoxy-substituted derivatives, or mixtures thereof, which are liquids at or about 20° C., which are substantially water-immiscible, and in which valeric or caproic acids are at least partially soluble. Examples of suitable solvents include, but are not limited to: hexane, n-heptane, cyclohexane, dichloromethane, benzene, toluene, o-xylene, m-xylene, butylbenzenes, diethylbenzenes, diisopropylbenzenes, ethylbenzene, isopropylbenzene, anisole, chlorobenzene, bromobenzene, propylbenzene, 1-bromonaphthalene, 1-chloronaphthalene, 1-methylnaphthalene, and mixtures thereof. Aromatic solvents are preferred, with toluene and benzene being the most preferred.

Suitable extraction-enhancing acids are at least partially soluble in the organic solvent and include $C_2$–$C_{10}$ carboxylic acids, other than caproic or valeric acids, and their derivatives, and alkyl or aryl sulfonic acids and their derivatives. Specific examples include acetic acid, propionic acid, butyric acid, isobutyric acid, 4-tolylacetic acid, cyclohexanecarboxylic acid, benzoic acid, and p-toluenesulfonic acid. Carboxylic acids are preferred.

In the process of this invention, the concentration of the extraction-enhancing acid in the extracting solvent is at least 0.01 wt. %, up to the solubility limit of the acid in the extracting solvent, or the concentration at which the aqueous and organic phases become miscible, whichever is less. The extraction-enhancing acid may be added to the system as a component of either organic extractant or aqueous feed and then distribute itself between the two phases, depending on its relative solubility in each phase. Normally the organic solvent is used in amount such that the ratio of solvent to aqueous solution is 0.5 to 2.5. Often, especially if the dicarboxylic acid is prepared by the use of a Group VIII metal catalyst by the reaction of CO and an olefin, the aqueous solution will contain Group VIII compounds. These compounds are also extracted by the organic solvent.

The effectiveness of a given solvent for extraction of valeric or caproic acids from an aqueous solution, at a given solution composition and given temperature, was characterized by a distribution coefficient defined as:

$$K_d = \frac{[\text{concentration of Valeric or Caproic Acid in Organic Phase}]}{[\text{concentration of Valeric or Caproic Acid in Aqueous Phase}]}$$

Ideally, $K_d$ represents the distribution of valeric or caproic acids in the aqueous and organic phases at equilibrium after infinitely long contact time. In practice, the approach to equilibrium is rapid, and $K_d$ is taken here to represent the concentration ratio at the time the phases are separated. The larger $K_d$, the more effective the extraction process and the fewer extraction stages required to reduce the aqueous valeric or caproic acid concentration to a given level.

The process may be carried out as a batch process, or continuously in a countercurrent extractor. The heavier phase would normally be introduced to a countercurrent reactor at the elevated end, and the lighter phase introduced at the lower end.

EXAMPLE 1

An aqueous feed containing 3.5% valeric acid (VA) and 21–24% methyl glutaric acid (MGA) was repeatedly extracted four times using toluene (TOL) containing 0.5, 1.0, 2, and 5% acetic acid (HOAc). The final aqueous concentrations of VA were, respectively, 0.074%, 0.060%, 0.043%, and 0.032%. Distribution coefficients were determined from the aqueous and organic VA concentrations at each extraction stage. Their values were in the order of the acetic acid concentration of the toluene extractant used. The concentration of acetic acid in the aqueous phase increased with each repeated extraction. Example 1 is summarized in Table 1.

TABLE 1

| Run Number | HOAc % in TOL. | Ext. Stage # | TOL. VA % | AQ. VA % | VA Dist. Coeff. | MGA % AQ. |
|---|---|---|---|---|---|---|
| 1 | 0.5 | 1 | 3.503 | 0.908 | 3.858 | 23.24 |
|   |   | 2 | 0.703 | 0.328 | 2.143 | 22.38 |
|   |   | 3 | 0.193 |   |   |   |
|   |   | 4 | 0.074 | 0.074 | 1.000 | 23.63 |
| 2 | 1 | 1 | 3.601 | 0.919 | 3.918 | 22.8 |
|   |   | 2 | 0.634 | 0.341 | 1.859 | 21.32 |
|   |   | 3 | 0.175 | 0.148 | 1.182 | 20.66 |
|   |   | 4 | 0.085 | 0.060 | 1.417 | 23.38 |
| 3 | 2 | 1 | 3.43 | 0.857 | 4.002 | 20.97 |
|   |   | 2 | 0.632 |   |   | 20.96 |
|   |   | 3 | 0.186 | 0.111 | 1.676 | 24.05 |
|   |   | 4 | 0.074 | 0.043 | 1.721 | 24.49 |
| 4 | 5 | 1 | 3.563 | 0.856 | 4.162 | 28.13 |
|   |   | 2 | 0.861 | 0.295 | 2.919 | 20.52 |
|   |   | 3 | 0.23 | 0.093 | 2.473 | 22.78 |
|   |   | 4 | 0.071 | 0.032 | 2.219 | 20.44 |

EXAMPLE 2

A Karr column equipped with reciprocating perforated plates was used to perform two series of continuous countercurrent extractions of valeric acid from an aqueous solution containing valeric acid and adipic acid (AA) using toluene as the extracting solvent. The Karr column is a commercial design of a column for continuous extraction. Data of the two series of experiments are shown in Table 2 below. Extraction of valeric acid was significantly enhanced by the presence of a carboxylic acid in the toluene extractant, or the aqueous feed, or both. In some runs, the final VA in the aqueous stream was below the 2 ppm detection limit. Runs 1A, 2A, 3A, 4A and 5A are control runs. In runs 1A through 3B the solvent to feed ratio was 1, and in 4A through 5B this ratio was 0.8.

TABLE 2

| Run Number |   | Aqueous Stream Composition | |
|---|---|---|---|
|   |   | Feed % | Raffinate ppm |
| 1A | AA | 22.6 | 25.3 |
|   | VA | 1.68 | 200 |
|   | Propionic | 0 | 0 |
| 1B | AA | 24.8 | 24.3 |
|   | VA | 1.53 | 8 |
|   | Propionic | 3.56 | 4.0 |
| 1C | AA | 24.5 | 23.8 |
|   | VA | 1.56 | 12 |
|   | Propionic | 6.0 | 5.0 |
| 2A | AA | 25.6 | 25.3 |
|   | VA | 1.68 | 200 |
|   | Butyric | 0 | 0 |
| 2B | AA | 25.0 | 24.9 |
|   | VA | 1.68 | 0 |
|   | Butyric | 3.0 | 0.5 |
| 3A | AA | 25.6 | 25.3 |
|   | VA | 1.68 | 200 |
|   | Benzoic | 0 | 0 |
| 3B | AA | 24.3 | 23.7 |
|   | VA | 1.6 | 98 |
|   | Benzoic | 4.9 | 0.16 |
| 4A | AA | 25 | 26.8 |
|   | VA | 233 | 1000 |
|   | Propionic | 0 | 0 |
| 4B | AA | 24.2 | 24.4 |
|   | VA | 2.35 | 300 |
|   | Propionic | 2 | 1.1 |
| 4C | AA | 24.6 | 24.1 |
|   | VA | 2.17 | 0 |
|   | Propionic | 5.0 | 2.8 |
| 5A | AA | 23.9 | 25.4 |
|   | VA | 2.15 | 900 |
|   | Butyric | 0 | 0 |
| 5B | AA | 25.3 | 26.4 |
|   | VA | 2.19 | 0 |
|   | Butyric | 5.0 | 0.9 |

EXAMPLE 3

Two sets of extractions were performed at 65° C. in which a 20% (by wt.) solution of adipic acid in water containing either 220 ppm or 1000 ppm valeric acid was extracted with a small amount of toluene. One set contained 1% isobutyric acid to enhance the extraction whereas the other had no isobutyric acid. The toluene phase was removed after extraction, then analyzed and the $K_d$ for VA and isobutyric calculated. The data from these experiments are shown in Table 3. As can be seen from this Table, the Distribution Coefficient ($K_d$) for valeric acid is clearly enhanced by the addition of 1% isobutyric acid at both levels of valeric acid in the feed.

TABLE 3
Extraction of Valeric Acid and Isobutyric Acid

| Ingredients: | Analysis (wt. %) Tol. Phase | Calculated (wt. %) Aq. Phase | $K_d$ |
|---|---|---|---|
| Experiment #1: (Control) | | | |
| 100.09 gms adipic acid | — | 20.01 | |
| 400.09 gms water | — | | |
| 0.1120 gms valeric acid | 0.0242 | 0.0222 | 1.09 |
| 4.3455 gms toluene | Balance | | |
| Agitated 5 min at 65° C. | | | |
| Experiment #2: (Control) | | | |
| 100.18 gms adipic acid | — | 19.90 | |
| 402.70 gms water | — | | |
| 0.4919 gms valeric acid | 0.0990 | 0.0969 | 1.02 |
| 4.3790 gms toluene | Balance | | |
| Agitated 5 min at 65° C. | | | |
| Experiment #3: | | | |
| 100.09 gms adipic acid | 0.0625 | 19.81 | 0.0032 |
| 400.04 gms water | — | | |
| 0.1139 gms valeric acid | 0.0418 | 0.0222 | 1.88 |
| 5.00 gms isobutyric acid | 0.9090 | 0.982 | 0.92 |
| 4.3564 gms toluene | Balance | | |
| Agitated 5 min at 65° C. | | | |
| Experiment #4: | | | |
| 100.20 gms adipic acid | 0.0855 | 19.81 | 0.0043 |
| 400.00 gms water | — | | |
| 0.5201 gms valeric acid | 0.2170 | 0.1028 | 2.11 |
| 5.00 gms isobutyric acid | 1.0320 | 0.9796 | 1.04 |
| 4.4520 gms toluene | Balance | | |
| Agitated 5 min at 65° C. | | | |

We claim:

1. A process for the purification of an aqueous solution containing a dicarboxylic acid selected from the group consisting of adipic acid, methyl glutaric acid and a monocarboxylic acid selected from the group consisting of valeric acid and caproic acid which comprises extracting the monocarboxylic acid with an organic solvent for monocarboxylic acid that is substantially water-immiscible and selected from the group consisting of hexane, n-heptane, cyclohexane, dichloromethane, benzene, toluene, o-xylene, m-xylene, butylbenzenes, diethylbenzene, anisol, chlorobenzene, bromobenzene, propylbenzene, 1-bromonaphthalene, 1-chloronaphthalene, 1-methylnaphthalene and mixtures thereof containing an effective amount of an extraction-enhancing acid that is soluble in the organic solvent and selected from the group consisting of acetic acid, propionic acid, butyric acid, 2-methyl butyric acid, isobutyric acid, 4-tolylacetic acid, cyclohexanecarboxylic acid, benzoic acid, benzenesulfinic acid, p-toluenesulfonic acid and 2-tolueneboronic acid.

2. The process of claim 1 in which the organic solvent has 6 to 12 carbon atoms.

3. The process of claim 1 in which the extraction-enhancing acid is selected from the group consisting of monocarboxylic acids and sulfonic acids.

4. The process of claim 3 in which the extraction-enhancing acid contains 2 to 12 carbon atoms.

5. The process of claim 1 in which the extraction takes place under conditions where the organic solvent is dispersed in the aqueous solution.

6. The process of claim 1 in which the extraction is continuous with countercurrent flows of immiscible phases.

7. The process of claim 1 in which the aqueous solution also contains a Group VIII metal compound, and the Group VIII metal compound is also extracted by the organic solvent.

8. The process of claim 1 in which the dicarboxylic acid is adipic acid, the acid to be extracted is valeric acid, the organic solvent is toluene and the extraction-enhancing acid is isobutyric acid.

9. The process of claim 1 in which the extraction-enhancing acid is present in the extraction solvent in the amount of at least 0.01 wt. % and not more than the solubility limit of the acid in the solvent or the concentration at which the aqueous and organic phases become miscible, whichever is less.

* * * * *